United States Patent

Henssge et al.

[11] Patent Number: 5,217,498
[45] Date of Patent: Jun. 8, 1993

[54] TIBIAL COMPONENT OF A KNEE JOINT PROSTHESIS

[75] Inventors: Ernst J. Henssge; Wolfgang Köller; Pavel Dufek, all of Lübeck; Jörg Scholz, Berlin, all of Fed. Rep. of Germany

[73] Assignee: S & G Implants GmbH, Lubeck, Fed. Rep. of Germany

[21] Appl. No.: 887,423

[22] Filed: May 21, 1992

Related U.S. Application Data

[62] Division of Ser. No. 629,231, Dec. 17, 1990, abandoned.

[30] Foreign Application Priority Data

Apr. 4, 1990 [EP] European Pat. Off. ......... 90106470

[51] Int. Cl.⁵ .................................................. A61F 2/28
[52] U.S. Cl. .......................................... 623/20; 623/18
[58] Field of Search .................... 623/16, 18, 20, 23

[56] References Cited

U.S. PATENT DOCUMENTS

| 3,067,740 | 12/1962 | Haboush | 623/23 |
| 4,822,362 | 4/1989 | Walker et al. | 623/20 |
| 4,863,474 | 9/1989 | Brown | 623/23 |
| 5,021,063 | 6/1991 | Tager | 623/23 |

FOREIGN PATENT DOCUMENTS

| 0664686 | 3/1988 | Switzerland | 623/18 |
| 8502535 | 6/1985 | World Int. Prop. O. | 623/18 |

Primary Examiner—David Isabella
Attorney, Agent, or Firm—Todd A. Dawson

[57] ABSTRACT

In a tibial portion of a knee joint endoprosthesis with a securing shank (10) to be inserted into the medullar cavity of the tibia, which, on one end, is provided or not with a tibia condyle terminal plate for the attachment of the articular parts of the prosthesis, the securing shank (10), in order to achieve a firm fit of the implant after the implantation, comprises a cylindrical sleeve (11) that is insertable into a cylindrical slotted drilled hole (201) of the tibia with an interior (12) accommodating the spongiosa nucleus (205) of the slotted drilled hole (201), and is fabricated from a metallic material or some other suitable, body-compatible material, while the securing shank (60) is disposed at a right angle to the terminal plate (20) extending parallelly to the horizontal or slightly inclined ostectomy area (206) (FIG. 1).

3 Claims, 5 Drawing Sheets

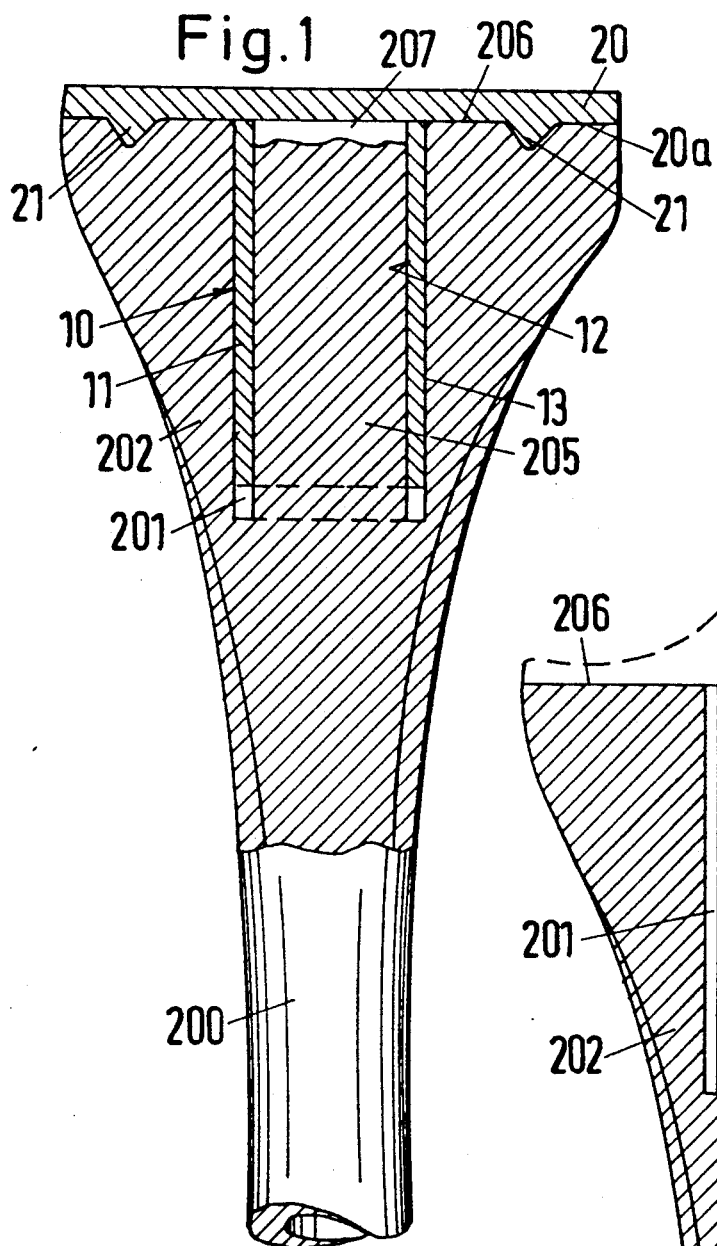
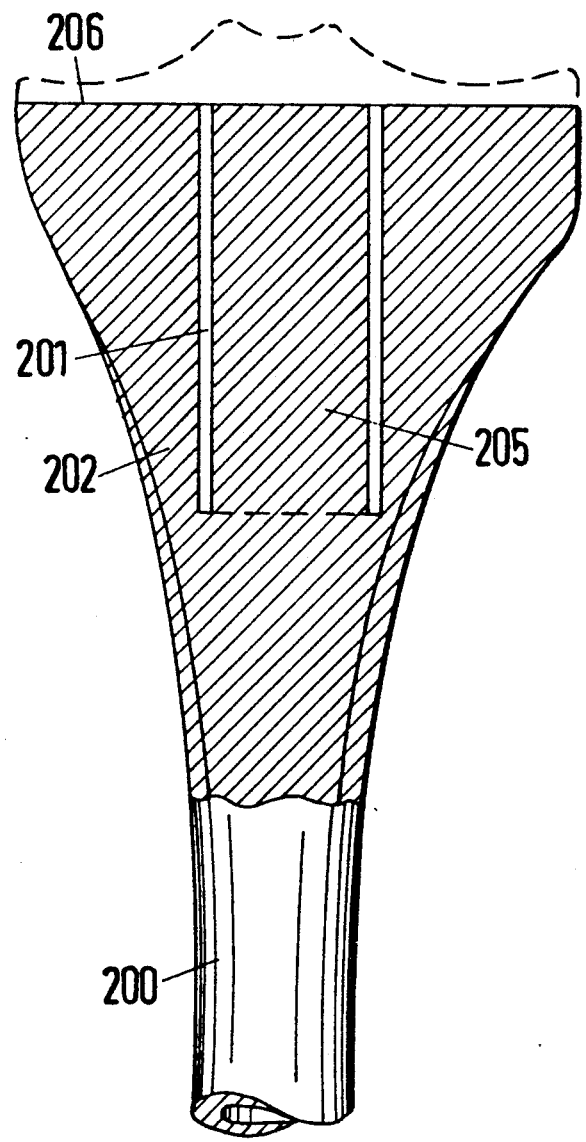

TIBIAL COMPONENT OF A KNEE JOINT PROSTHESIS

This application is a division of application Ser. No. 07/629,231 filed Dec. 17, 1990, now abandoned.

BACKGROUND OF THE INVENTION

The present invention relates to a tibial portion of a knee joint endoprosthesis with a securing shank to be inserted into the medullar cavity of the tibia, which, on one end, is provided with or is without a tibia condyle terminal or closing plate for the attachment of the articular parts of the prosthesis.

From the DE-A-36 27 097, a shank that is insertable into the medullar space of a bone for articular endoprostheses is known, which, over at least a part of its length, is constructed so as to be hollow and is provided with at least one longitudinal slot which terminates in the cavity and forms a connection of the cavity with the surrounding area. Due to such a construction of a securing shank for articular endoprostheses, it is intended to approximate their natural resilience to that of the natural bone.

An endoprosthesis for a knee joint, comprising a tibial portion to be secured by means of a shank with a central web and with gliding surfaces disposed on both sides of the latter, and a femoral portion to be likewise secured by means of a shank which is provided with two skids that bridge the web and are supported on the gliding surfaces, wherein the tibial and the femoral portions are movably interconnected by means of a pivot located transversally to the web eccentrically to the tibia shank, is known from the DE-A-25 49 819. In this endoprosthesis, the pivot is movably inserted eccentrically against the convexity of the gliding surface toward the rear in the web in its longitudinal axis, while the ends of the pivot engage with play into guide grooves in the skids extending roughly parallelly to the lower skid surface and which are open toward the top, whereas the web and the spacing of the skids toward the rear are constructed so as to become wider in a manner known per se. Accordingly, this endoprosthesis of a knee joint is constructed in such a way that the articular movements of a natural knee joint are retained or very nearly retained, the femoral portion being able during the bending procedure to lengthen rearwardly in a rolling and gliding manner to an extent which differs from case to case and, in the process, also allows a rotary movement of the thighs relative to each other to take place.

A securing shank for a tibial portion of a knee joint endoprosthesis connected or to be connected to it, which, over its length, possesses a constant or, in the direction of its free end, a conically narrowing cross-sectional course, is known from the DE-A-26 60 458. In this shank, the longitudinal portion engaging into the medullar cavity, at least over a part of the shank length, has a cross-sectional configuration in the form of an irregular triangle with rounded edges and outwardly curved sides. On account of such a shank construction, a torsionally safe position of the tibial portion with very slight play is possible which, over and above that, corresponds to the position of the natural tibial tabula.

In comparison with the known securing shanks for knee joint endoprostheses, it is the object of the present invention to provide a tibial portion for a light-weight securing means which meets the biomechanical requirements of a knee joint endoprosthesis in the tibial bone with the possibility of achieving a vascularization of the blood vessels in the bone up to the medullar cavity, in which, moreover, the tibial portion has to possess large areas for absorbing flexural forces.

SUMMARY OF THE INVENTION

As compared with the known securing shanks of knee joint endoprostheses which are constructed with solid walls and in which the interspace or clearance formed subsequent to the implantation between the securing shank and the osseous material has to be filled with a cement material, due to the construction according to the invention of the tibial portion, a perfect implantation with a firm fit of the securing shank is obtained. Owing to the fact that the securing shank is constructed in a sleeve-like manner and the same is, for the purpose of the implantation, introduced into a cylindrical, slotted drilled hole of the tibia, the interior of the sleeve is filled by the spongiosa nucleus retained by the cylindrical, slotted drilled hole. If, over and above that, the sleeve is provided with a number of regularly or irregularly arranged perforations in its cylindrical casing, then the possibility of the vascularization of the blood vessels into the bone is ensured. The slotted drilled hole to be constructed in the tibia, in relation to the dimensions of the sleeve-like-constructed securing shank, is dimensioned in such a way that the securing shank is retained in the slotted drilled hole with a snug fit so that an additional cementing-in after the effected implantation is no longer necessary.

To the end that the terminal or closing plate mounted on the securing shank is seated firmly on the ostectomy area of the bone, subsequent to the slotted bore having been drilled into the tibia within the upper area of the spongiosa nucleus remaining in the center of the slotted drilled hole, a section is removed, whereby, subsequent to the insertion and driving in of the securing shank into the cylindrical, slotted drilled hole, with its wall area facing the ostectomy area, rests on the ostectomy area with its entire surface.

In order to achieve a firm fit of the implanted securing shank, the terminal plate, on its wall area facing the ostectomy area, is provided with a plurality of bone-locking studs or pegs, which, subsequent to the insertion and pressing-in of the securing shank, engage into the bone within the ostectomy area.

The tibial portion of the knee joint endoprosthesis is characterized in that the hollow securing shank of the prosthesis to be inserted into the tibial medullar cavity is rigidly or variably connected to a transversally oval upper terminal plate for the condyle of the tibia and terminates in an asymmetrical fashion in the downward direction in that a segment of the tubular securing shank located at the rear/on the outside terminates above the terminal point and which possesses a flexure that is convex while being forwardly and medially directed. Due to this construction, an easy securing of a knee joint endoprosthesis in the tibial bone meeting biomechanical requirements can be achieved. This is done in that the hollow securing shank is provided with curvatures, from which results that the securing shanks for the right and the left tibia are constructed in a mirror-inverted manner.

The hollow securing shank may optionally be provided with a conical cavity located centrally at the top, into which various coupling members for the knee joint can be introduced, or, for the purpose of saving weight, also be rigidly connected to the respective tibial portion at the option of the manufacturer. The outward surface texturing and the inward texturing in the cavity is subject to the choice of the manufacturer and should be such as to encourage the osseous integration.

If the securing shank is intended to be fixed by means of osteocementum in the tibia, the interior of the securing shank will have to remain sealed in the downward direction. If this is not the case, the lower aperture should remain open in order to preserve bones, i.e. spongiosa portions in the interior of the securing shank so as to thereby ensure the fixation of the securing shank also from the inside. In order to ensure the nutrition of the bone, the hollow securing shank with the lower aperture left open is provided with slits in its wall for blood vessels to pass through so as to render possible the nutrition of the bone also in the cavity of the securing shank.

The upwardly directed terminal plate of the endoprosthesis provided on the securing shank is rearwardly inclined through 2° to 4°. This form of construction encourages the rolling-gliding behavior of the knee joint in imitation of the normal physiological conditions.

The connection to the thigh can be variably effected according to the state of the art with the aid of coupling systems or ligamental bridging. That is why the terminal plate of the endoprosthesis directed toward the knee joint has to be constructed at the option of the manufacturer in such a way that e.g. polyethylene gliding areas and/or web-like projections with a coupling possibility and/or exit slots for the ligamental prostheses integrated in to the endoprosthesis are provided.

BRIEF DESCRIPTION OF THE DRAWINGS

Embodiments of the invention are explaiend in greater detail in the following with the aid of the drawings. Thus FIG. 1 shows, partly in a view and partly in a vertical section, a shank for the tibial portion of a knee joint endoprosthesis implanted into the tibia, FIG. 2 shows, partly in a view and partly in a vertical section, a tibia with a cylindrical, slotted drilled hole for accommodating the sleeve-like-constructed securing shank.

DETAILED DESCRIPTION OF THE PREFERRED EMBODIMENT

Figure 3:
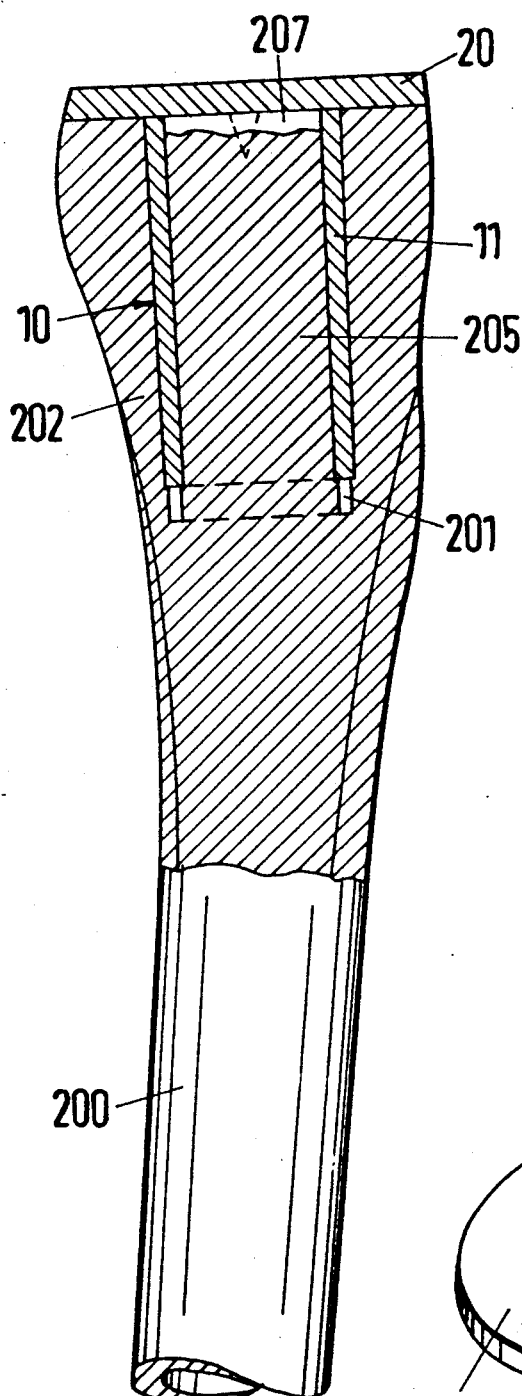
FIG. 3 shows, in a medial-lateral view, the tibia with the implanted securing shank.
Figure 4:
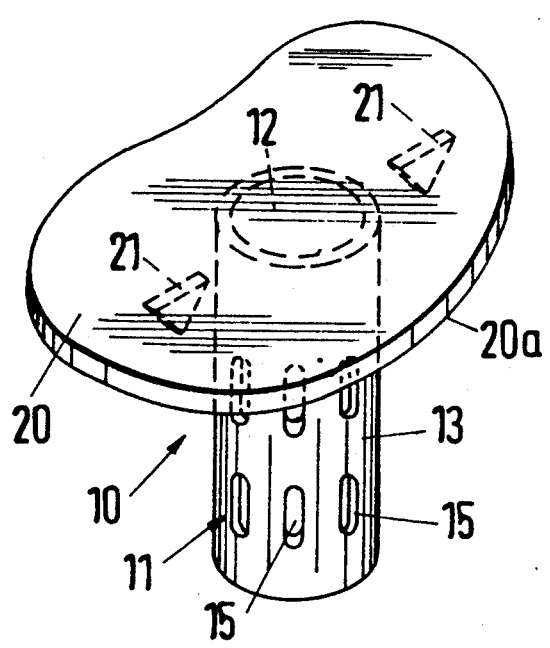
FIG. 4 shows, in a diagrammatical view, the securing shank with its upper terminal plate.

The securing shank (10) for a tibial portion of a knee joint endoprosthesis which is to be inserted into the medullar cavity of the tibia is shown in FIGS. 1, 3 and 4. This securing shank 10 comprises a cylindrical sleeve 11 fabricated from a metallic material or some other suitable body-compatible material. The sleeve interior (12) and the sleeve casing forming the outer wall (13) are shown in FIG. 1.

On one of its two extremities, the sleeve 11 is provided with a terminal or closing plate 20, the wall area 20a of which that faces the sleeve 11 is provided with a plurality of bone-locking studs or pegs 21. A torsional stability of the securing shank 10 following the effected implantation is already achieved when the terminal plate 20, on its wall area 20a facing the ostectomy area is provided with a bonelocking stud or peg 21.

The implantation of the securing shank 10 is effected in a cylindrical, slotted drilled hole 201 constructed in the tibia 200 (FIG. 2). Subsequent to this cylindrical slotted drilled hole 201 having been produced, a central nucleus 205 of the spongiosa 202 remains. The diameter of this slotted drilled hole 201 and its dimensions are, in relation to the sleeve 11 of the securing shank 10, such that, subsequent to the insertion or driving-in of the sleeve 11 into the slotted drilled hole 201, the sleeve 11 is retained with a snug fit in the slotted drilled hole 201. By preference, the wall portion formed by the slotted drilled hole 201 is of a width which is somewhat smaller than the material thickness of the sleeve 11 so that, subsequent to the implantation of the securing shank 10 in the spongiosa 202 and in the medullar cavity of the tibia 200, no interspace or clearance is obtained between the sleeve casing 13 and the osseous material which has to be filled or sealed with cement material. The length of the slotted drilled hole 201 is preferably dimensioned so as to be somewhat larger than the length of the sleeve 11 of the securing shank 10 so that, after the effected implantation, the terminal plate 20 rests with its wall area 20a on the ostectomy area 20b with its entire surface.

After the implantation has been performed, the spongiosa nucleus 205 obtained by means of the slotted drilled hole 201 fills the interior 12 of the sleeve 11. In this case the spongiosa nucleus 205 may extend over the entire length of the sleeve and fill the entire sleeve interior 12. However, over and above that, there also exists the possibility of constructing, in the interior 12 of the sleeve 11, an upper, spongiosa-free space 207 so that the spongiosa nucleus 205 located in the sleeve interior 12 has a shorter length when compared with the length of the sleeve 11. The construction of an upper spongiosa-free space 207 in the interior 12 of the sleeve 11 following the effected implantation of the securing shank 10 into the tibia 200 ensures the full-surface abutment of the terminal plate 20 against the ostectomy area 206.

In order to ensure the nutrition of the bone or of the spongiosa in the interior of the sleeve 11 after the securing shank 10 has been implanted, the casing 13 of the sleeve 13 is provided with regularly or irregularly disposed perforations 15 (FIG. 4).

Figure 5:
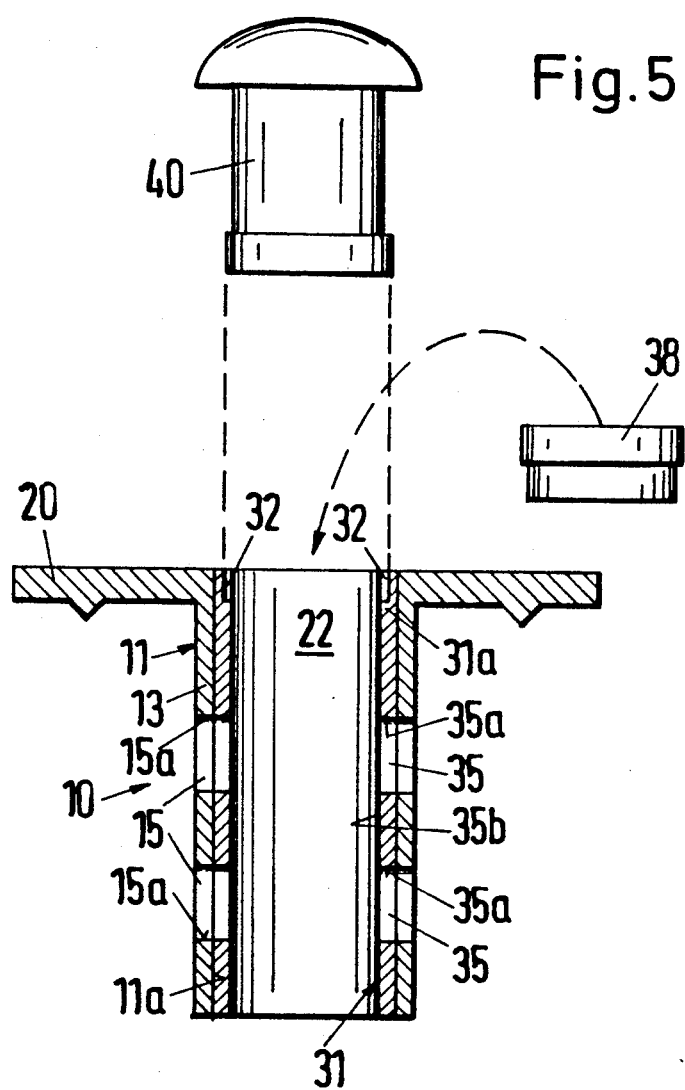
FIG. 5 shows, in a vertical section, a further embodiment of a tibia securing shank.

According to a further embodiment as per FIG. 5, the rims 15a which delimit the individual perforations 15 constructed in the cylindrical casing 13 of the sleeve 11 are constructed in a knife blade-like manner and have the effect of a cutting knife. The sleeve 11 of the securing shank 10 is provided in its interior 12 with a further shaped member 31 bearing against the sleeve inner wall area 11a which is fabricated from a metallic material or some other suitable, body-compatible material. This sleeve-like shaped member 31 is provided with a plurality of perforations 35 that coincide with the perforations 15 of the sleeve 11, while the rims 35a which delimit the individual perforations 35 of the sleeve-like shaped member 31 are likewise constructed in the manner of a knife blade and have the effect of a cutting knife. The size and the configuration of these perforations 35 correspond in this case to those of the perforations 15 constructed in the casing 13 of the sleeve 11. The implantation of a thusly constructed securing shank 10 is likewise carried out in a cylindrical, slotted drilled hole 201 constructed in the tibia 200, said hole being dimensioned in such a way that the sleeve 11 with its internally located sleeve-like shaped member 31 is insertable into this slotted drilled hole 201. In the implanted state, the sleeve-like shaped member 31 then assumes a position relative to the sleeve 11 in which the perforations 15 of the sleeve 11 coincide with the perforations 35 of the sleeve-like shaped member 31. A securing shank 10 constructed and implanted in this manner ensures an adequate nutrition of the bone since the mutually coinciding perforations 15,35 render possible the passing through of blood vessels so that the bone in the interior 12 of the sleeve 11 can be adequately nourished. To this is added the circumstance that a coalescence of the bone with that bone portion which is located in the interior 12 of the sleeve 11 is possible via these perforations.

The internal sleeve-like shaped member 31 is, with its upper end 31a, extended as far as into the area of an opening 22 constructed centrally in the terminal plate 20. In addition, the shaped member 31, on its upper end, is provided with engagement cams 32 constructed in its inner wall area 35a for a tool 40 which can be applied to the sleeve-like shaped member 31 and be brought into operative connection with the same so as to render possible a rotation of the sleeve-like shaped member 31 about its central longitudinal axis. As an engagement tool 40, a key as depicted in FIG. 5 can be used. In the implanted state, the drilled opening 22 provided in the upper terminal plate 20 is sealed by means of a closing cap 38. This rotational possibility of the sleeve-like shaped body 31 is of advantage inasmuch as the possibility thereby exists of effortlessly removing an implanted securing shank 10 again if this were to prove necessary. By merely rotating the sleeve-like shaped member 31, the blood vessels which have passed through the perforations 15,35 and the osseous substance which has grown through the perforations are severed, this severance being assisted by the knife blade-like construction of the marginal areas of the perforations 15,35. The sleeve 11 of the securing shank 10 has a circular cross-section.

A further embodiment of a tibial portion of a knee joint endoprosthesis with a securing shank 110 is illustrated in the FIGS. 6 thru 10.

The securing shank 110 is constructed so as to be tubular and comprises a sleeve 111 that is fabricated from a metallic material or some other suitable, body-compatible material. The lower free end of the sleeve 111 is identified with 111a and the upper end with 111b. On its upper end 111b, the sleeve 111 bears a transversally oval tibia condyle plate 120 which is rigidly or detachably connected to the securing shank 110.

Figure 6:
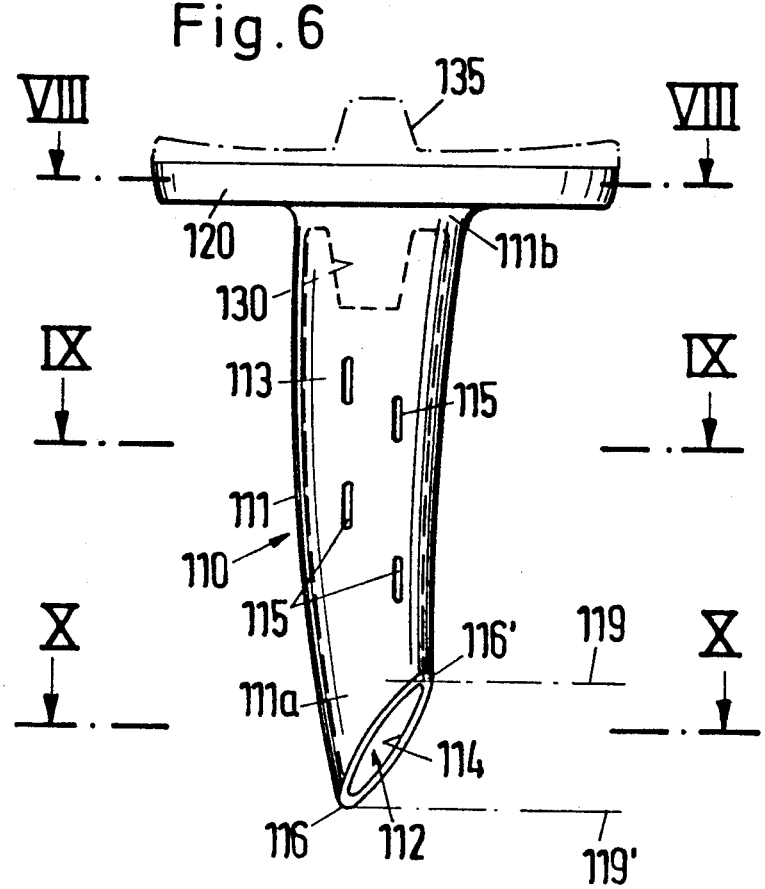
FIG. 6 shows a view of a further embodiment of a securing shank with a forwardly and medially directed flexure with a plate terminating in the upward direction.
Figure 7:
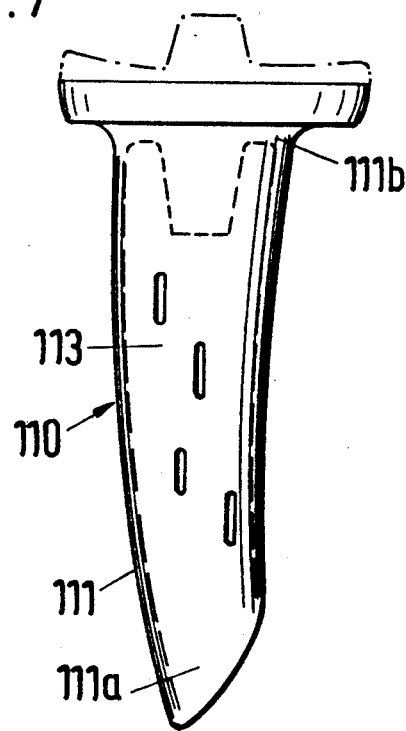
FIG. 7 shows a view of the securing shank according to the FIG. 6 with the rearwardly directed inclination of the tibia condyle terminal plate.
Figure 8:
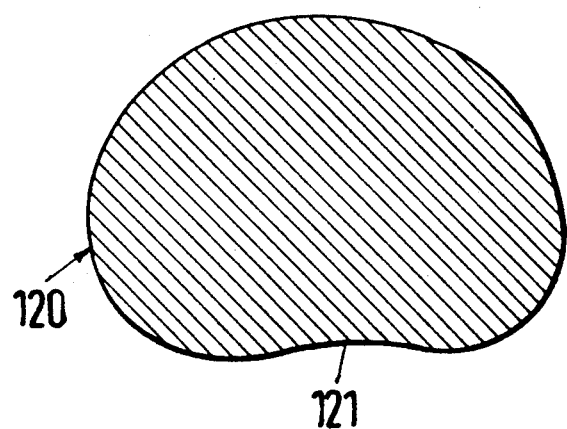
FIG. 8 shows a horizontal section through the terminal plate with its transversally oval, kidney-shaped cross-sectional surface in the direction of Line VIII—VIII in FIG. 6.
Figure 9:
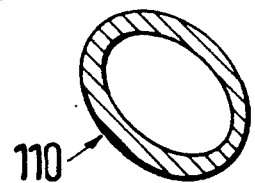
FIG. 9 shows a horizontal section through the tubular securing shank in the direction of Line IX—IX in FIG. 6.

At its free end 111a, the sleeve 111 of the securing shank 110 terminates in an asymmetrical fashion and, while forming an oval surface of cut 114, is cut obliquely in such a way that a rearwardly/externally located segment of the securing shank 110 terminates above the point-like end 116 of the securing shank 110 (FIGS. 6, 7 and 9).

In addition, the sleeve 111 of the securing shank 110 exhibits a forwardly and medially directed convex flexure. FIG. 6 shows a view of the securing shank 110 for the left knee; for the right knee, a mirror-inverted construction of the securing shank 110 would then have to be produced. In the FIGS. 6 and 7, at 135, the possibility of the conical coupling of two parts and the possibility of the construction of the gliding surface with web for a coupling connection is indicated. For this purpose, the securing shank 110 is, on its upper end 111b, centrally provided with a conical recess 130 for the accommodation of the coupling members of the knee joint.

The terminal plate 120 on the upper end 111b of the sleeve 111 possesses a rearwardly directed inclination of 2° thru 4°.

Figure 10:
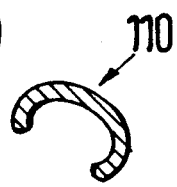
FIG. 10 shows a horizontal section in the direction of Line X—X in FIG. 6.

The free end 111a of the securing shank 110 is constructed so as to be open (FIG. 10). The nutrition of the bone also in the interior of the sleeve 111 is ensured hereby. Beyond that, there also exists the possibility of constructing the free end 111a of the securing shank 110 so as to be closed.

The FIG. 9 shows a cross-section through the sleeve 111 of the securing shank 110 with its inclined oval surface of cut 114, whereas FIG. 10 reproduces a cross-section within that section which is located in the asymmetrical portion of the cavity of the sleeve 111 and only in front and medially still represents one half or two thirds of the sleeve proportion.

In the cross-sections indicated with I, II and III in the FIG. 6, the securing shank 110 possesses cross-sectional area dimensions at a ratio of 6.5:2:0.5, while it is also possible to select other ratios for these three cross-sectional dimensions relative to each other.

The sleeve casing 113 of the securing shank 110 is provided with a plurality of e.g. slot-like perforations 115.

Due to the oblique termination of the sleeve 111 of the securing shank 11, terminal areas 116,116' result at the front and at the rear which are located in different planes. The planes in which these terminal areas 116,116' are located, are indicated in FIG. 6 with 119,119'. According to FIG. 8, the terminal plate 120 which posseses a transversally oval, kidney-shaped cross-sectional area, within its rearward area, is provided with a centrally located cutout 121 which is connected to the rear crucial ligament which is left in its place or to a ligamental prosthesis. This kidney-shaped cutout 121 corresponds to the rear crucial ligament which is possibly left as it is or which can be connected to a ligamental substitute—ligamental prosthesis—to be firmly secured at this point. In this connection the kidney-shaped cutout prevents the natural or artificial ligament from having to be bent about an edge.

What is claimed is:

1. A tibial portion of a knee joint endoprosthesis with a securing shank to be inserted into the spongiosa bone of the medullar cavity of the tibia, which, on one end is provided with a tibia condyle terminal plate for the attachment of the articular parts of the prosthesis, characterized in that the securing shank comprises a tubular sleeve that is insertable into a matching, slotted drilled hole of the tibia with an interior accommodating the spongiosa bone, the tubular sleeve being provided with a plurality of regularly or irregularly disposed perforations formed in a wall of the sleeve, wherein edges of the perforations constructed in the wall of the sleeve being constructed in a knife blade-like manner, and a second sleeve carried within the first mentioned sleeve, said second sleeve being provided with a plurality of perforations which coincide with the perforations of the first mentioned sleeve, the perforations in said second sleeve defining knife blade-like edges.

2. The tibial portion of a knee joint of claim 1 wherein the second sleeve further includes engagement cams adapted for operative engagement with a tool for rotating said second sleeve relative to the first mentioned sleeve.

3. The tibial portion of a knee joint of claim 1 further including a cap for seating within said second sleeve adjacent the plate such that said cap does not extend above said plate.

* * * * *